United States Patent [19]

Lieber

[11] Patent Number: 5,284,835
[45] Date of Patent: Feb. 8, 1994

[54] USE OF DILINOLEOYLPHOSPHATIDYLCHOLINE (DLPC) FOR TREATMENT AND PREVENTION OF CIRRHOSIS AND FIBROSIS IN THE LIVER

[76] Inventor: Charles S. Lieber, 6 Johnson Ave., Englewood Cliffs, N.J. 07632

[21] Appl. No.: 923,130

[22] Filed: Jul. 31, 1992

[51] Int. Cl.$^5$ .................................. A61K 31/685
[52] U.S. Cl. .................................. 514/76; 514/838
[58] Field of Search .................................. 514/76, 838

[56] References Cited

PUBLICATIONS

Chemical Abstracts 109: 66897y (1988).
Rojkind et al., Gastroent. 76:710–719 (1979).
Murata et al., Hepato–Gastroent. 31:158–161 (1984).
Martinez-Hernandez, Lab. Invest. 51:57–74 (1984).
Sakakibana et al., Virchows Arch. [PA] 408:219–228 (1985).
Chojkier et al., Hepatology 8:808–814 (1988).
Milani et al., Hepatology 10:84–92 (1989).
Friedmann et al., PNAS (USA) 82:8681–8685 (1985).
Clement et al., Hepatology 6:225–234 (1986).
Minato et al., Hepatology 3:559–566 (1983).
Moshage et al., Hepatology 12:511–518 (1990).
Casini et al., Hepatology 13:758–765 (1991).
Mak et al., Gastroenterology 87:188–220 (1984).
Mak et al., Hepatology 8:1027–1033 (1988).
Maruyama et al., Bioch. Biophy. Acta 658:124–131 (1981).
Maruyama et al., Life Scie. 30:1379–1384 (1982).
Yamada et al., Gastroent. 88:1799–1806 (1985).
Friedman, Hepatology 12:609–612 (1990).
Lieber et al., Hepatology 12:1390–1398 (1990).
Kuntz et al., Med. Welt 40:1327–1329 (1989).
Lieber et a l., in "Progress in Liver Diseases" pp. 253–272 (ed. Popper, Schiffer, Grune & Stratton, NY, vol. VIII, Chapter 14) 1986.

*Primary Examiner*—Leonard Schenkman
*Attorney, Agent, or Firm*—Allegretti & Witcoff, Ltd.

[57] ABSTRACT

This invention encompasses pharmaceutical compositions and a dietary supplement for treating or preventing alcoholic cirrhosis of the liver which comprises administering about 1 to 3 grams per day of dilinoleoylphosphatidylcholine (DLPC).

3 Claims, No Drawings

USE OF DILINOLEOYLPHOSPHATIDYLCHOLINE (DLPC) FOR TREATMENT AND PREVENTION OF CIRRHOSIS AND FIBROSIS IN THE LIVER

BACKGROUND OF THE INVENTION

1. Field of the Invention

This invention is in the field of prevention and treatment of liver cirrhosis.

2. Description of the Prior Art

Liver fibrosis, regardless of its cause, is characterized by marked accumulation of extracellular matrix in the perisinusoidal space (Rojkind M, Giambrone M. A., Biempica L. Collagen types in normal and cirrhotic liver. Gastroenterology 1979; 76: 710-719; Murata K, Kudo M, Onuma R, Motoyama T. Changes of collagen types at various stages of human liver cirrhosis. Hepato-Gastroenterology 1984; 31: 158-161). Many efforts have been made to identify the cellular sources of extracellular matrix proteins in intact liver. Some observations have suggested that parenchymal liver cells play a central role in the production of interstitial collagen (Martinez-Hernandez A. The hepatic extracellular matrix. I. Electron immunohistochemical studies in normal rat liver. Lab Invest 1984; 51: 57-74; Sakakibara K, Igarashi S, Hatahara T. Localization of type III procollagen aminopeptide antigenicity in hepatocytes from cirrhotic human liver. Virchows Arch [A] 1985; 408: 219-228; Chojkier M, Lyche K. D., Filip M. Increased production of collagen in vivo by hepatocytes and nonparenchymal cells in rats with carbon tetrachloride-induced hepatic fibrosis. Hepatology 1988; 8: 808-814). Other experiments, however, have led to the conclusion that hepatic extracellular matrix production is largely a function of mesenchymal liver cells (Milani S, Herbst H, Schuppan D, Hahn E. G., Stein H. In situ hybridization for procollagen types I, III and IV mRNA in normal and fibrotic rat liver: evidence for predominant expression in nonparenchymal liver cells. Hepatology 1989; 10: 84-92; Friedman S. L., Roll F. J., Boyles J, Bissell D. M. Hepatic lipocytes: the principal collagen-producing cells of normal rat liver. Proc Natl Acad Sci USA 1985; 82: 8681-8685). Lipocytes (fat-storing or Ito cells), the principal cells in the Disse space of the liver, were found to synthesize and release different types of collagen (Clement B, Grimaud J. A., Campion J. P., Deugnier Y, Guillouzo A. Cell types involved in collagen and fibronectin production in normal and fibrotic human liver. Hepatology 1986; 6: 225-234), and they are considered to play an important role in the development of alcohol-induced liver fibrosis (Minato Y, Hashamura Y, Takeuchi H. The role of fat-storing cells in Disse space fibrogenesis in alcoholic liver disease. Hepatology 1983; 3: 559-566). Previous studies have reported that acetaldehyde stimulates collagen production in vitro (Moshage H, Casini A, Lieber C. S. Acetaldehyde selectively stimulates collagen production in cultured rat liver fat-storing cells but not in hepatocytes. Hepatology 1990; 12: 511-518) and increases procollagen type I gene transcription in cultured lipocytes (Casini A, Cunningham M, Rojkind M, Lieber C. S. Acetaldehyde increases procollagen type I and fibronectin gene transcription in cultured rat fat-storing cells through a protein synthesis-dependent mechanism. Hepatology 1991; 13: 758-765). In vivo, the progression liver fibrosis was accompanied by the transformation of lipocytes to transitional cells in fatty livers with perivenular fibrosis or cirrhosis, with a significantly higher collagen score in the Disse space surrounding transitional cells compared with that surrounding lipocytes (Mak K. M., Leo M. A., Lieber CS. Alcoholic liver injury in baboons: transformation of lipocytes to transitional cells. Gastroenterology 1984; 87: 188-200; Mak K. M., Lieber C. S. Lipocytes and transitional cells in alcoholic liver disease: a morphometric study. Hepatology 1988; 8: 1027-1033). In addition to collagen production, collagen breakdown determines the degree of collagen accumulation. Collagenase activity is generally increased during the early stage of liver injury (Maruyama K, Feinman L, Okazaki I, Lieber C. S. Direct measurement of neutral collagenase activity in homogenates from baboon and human liver. Biochim Biophy Acta 1981; 658: 124-131). Previous studies revealed that fibrosis coincides with the state at which collagen breakdown slackens and stops keeping pace with increased production (Maruyama K, Feinman L, Fainsilber Z, Nakano M, Okazaki I, Lieber CS. Mammalian collagenase increases in early alcoholic liver diseases and decreases with cirrhosis. Life Science 1982; 30: 1379-1384). Therefore these findings suggested that studies of the production and regulation of collagenase activity during liver injury may be relevant to the elucidation of the pathogenesis of liver fibrosis.

Membrane alterations are a striking component of alcohol-induced liver injury (Yamada S, Mak K. M., Lieber C. S. Chronic ethanol consumption alters rat liver plasma membranes and potentiates release of alkaline phosphatase. Gastroenterology 1985; 88: 1799-1806). Phosphatidylcholine may directly influence membrane structures and provide a basis for some of the beneficial effects of essential phospholipids in the treatment of liver diseases (Kuntz E. Pilotstudie mit Polyenylphosphatidylcholin bei schwerer Leberinsuffizien. Med Welt 1989; 40: 1327-1329). Recently, it was reported that polyunsaturated lecithin (PUL) extracted from soybeans can prevent fibrogenesis in alcohol-fed baboons. None of the animals fed PUL progressed beyond the stage of perivenular fibrosis. Furthermore, when three of the ethanol-PUL-treated animals were no longer given PUL but continued to ingest the same amount of the ethanol-containing diet, they rapidly progressed to more severe stages of fibrosis, including cirrhosis, illustrating again the protective effect of PUL (Lieber C. S., DeCarli L. M., Mak K. M., Kim C. I., Leo M. A. Attenuation of alcohol-induced hepatic fibrosis by polyunsaturated lecithin. Hepatology 1990; 12: 1390-1398).

SUMMARY OF THE INVENTION

This invention encompasses pharmaceutical compositions containing dilinoleoylphosphatidylcholine (DLPC) and a method for using DLPC for prevention and treatment of liver cirrhosis and fibrosis.

Pharmaceutical agents and methods are particularly applicable for prevention and treatment of cirrhosis and fibrosis of the liver of individuals who consume excess alcohol.

DETAILED DESCRIPTION OF THE INVENTION

Characteristic features of alcoholic liver injury include scarring or fibrosis and striking membrane alterations, with associated phospholipid changes. To offset some of these abnormalities, studies were previously conducted in baboons fed a liquid diet supplemented with polyunsaturated lecithin for up to eight years with either ethanol (50% of total energy) or isocaloric carbohydrate (Lieber et al., supra, 1990). These animals were compared with another group of baboons fed an equivalent amount of the same diet (with or without ethanol), but devoid of lecithin. In the two groups, comparable increases in lipids developed in the ethanol-fed animals, but striking differences in the degree of fibrosis were seen. Whereas at least septal fibrosis (with cirrhosis in some) and transformation of their lipocytes into transitional cells developed in seven of the nine baboons fed the regular diet with ethanol, no cirrhosis or septal fibrosis developed in any of the animals fed lecithin. They also had a significantly lesser activation of lipocytes to transitional forms, the cells considered to be mainly responsible for the production of collagen in the fibrous tissue (Lieber C. S., Leo M. A. Interaction of alcohol and nutritional factors with hepatic fibrosis. In Progress in Liver Diseases. Popper H, Schaffner F (eds.), Grune and Stratton, New York, Vol. III, Chapt. 14, pp. 253-272 (1986); Friedman S. L. Acetaldehyde and alcoholic fibrogenesis: fuel to the fire, but not the spark. Hepatology 1990; 12: 609-612). The soybean lecithin extract used was rich in polyunsaturated phospholipids, including 55% to 60%, phosphatidylcholine (PC). To asses whether PC was the active agent, we now fed a more purified extract, comprising 94% to 96% PC. We found that the feeding of the lecithin extract rich in PC protected against alcohol-induced fibrosis and that, in cultured lipocytes, pure dilinoleoyl-PC (DLPC), the main PC species of the extract, selectively increased collagenase activity.

MATERIAL AND METHODS

In Vivo Studies. Thirty-three *Papio hamadryas* baboons (10 kg to 20 kg, eight males, twenty-five females) were studied in compliance with the Institution's guidelines for animal research and were given four different diets for up to 5 years. Ten were fed a regular nutritionally adequate liquid diet (Lieber et al., supra, 1990). Ten other animals were given the same diet except for isocaloric replacement of carbohydrate (50% of total energy) with ethanol.

Thirteen animals were fed the same diets, with ethanol (seven animals) or isocaloric carbohydrate (six controls), but supplemented with 2.8 g/1000 kcal of a lecithin (extracted from soybeans) obtained from Natterman and Co. (Cologne, Germany), and containing 94% to 96% PC of which the two major species are DLPC (40% to 52%) and linoleoyl-palmitoyl-PC (LPPC) (23% to 24%).

All animals either maintained or slightly gained weight, and their general appearance remained normal throughout the study.

Percutaneous liver biopsy specimens were obtained with the animals under ketamine anesthesia six hours after food withdrawal. Similar samples were taken from each of the groups. For light microscopy and electron microscopy, specimens were coded for blind reading and prepared and examined as described (Lieber C. S., Leo M. A., Mak K. M., DeCarli L. M., Sato S. Choline fails to prevent liver fibrosis in ethanol-fed baboons but causes toxicity. Hepatology 1985; 5: 561-575). The volume density of lipid droplets in lipocytes (Ito cells, fat-storing cells) in the perisinusoidal space and fibrous scars was estimated as reported in Mak et al., (supra, 1984), using electron micrographs of lipocytes (at $\times 12,500$ or $\times 20,000$ magnification). A point grid with 0.5 $\mu$m point-to-point distance was superimposed on the lipocytes, and the number of points overlying the lipid droplets was counted; this value was expressed as the percentage of the cell volume. As defined and validated in Mak et al., (supra, 1984), cells were considered to be lipocytes when the volume density of lipid droplets was greater than 20% of the cell volume; conversely, cells were considered to be transitional cells when the volume of lipid droplets was less than 20% of the cell.

In Vitro Studies. Lipocytes were isolated from Sprague-Dawley rats (500 gm to 700 gm body weight) that had free access to water and Purina Chow diet (Ralston Purina Co., St. Louis, Mo.). Nonparenchymal liver cells were isolated by the pronase-collagenase method of Knook, Seffelaar and de Leeuw (Knook D. L., Seffelaar A. M., de Leeuw A. M. Fat-storing cells of the rat liver: their isolation and purification. Exp. Cell Res. 1982; 139: 468-471), with minor modifications as described by Moshage, Casini and Lieber (Moshage et al., supra, 1990). After isolation, lipocytes were separated from other nonparenchymal cells, as described in Li J-J, Kim C-I, Leo M. A., Mak K. M., Rojkind M, Lieber C. S. (Polyunsaturat lecithin prevents acetaldehyde-mediated hepatic collagen accumulation by stimulating collagenase activity in cultured lipocytes. Hepatology 1992; 15: 373-381), seeded on plastic tissue-culture dishes at a starting density of $1 \times 10^5$ cells/ml and incubated at 37° C. in a 5% $CO_2$ air-humidified atmosphere. The medium was replaced 24 hours after plating and every 48 to 72 hours thereafter. Subcultures (passage 1 or 2) were obtained by trypsinization using a 0.025% trypsin solution containing 0.01% EDTA when the cells became confluent after 7 to 10 days. Lipocytes were identified by their typical stellate appearance under the phase-contrast microscope and the constant positive immunofluorescence staining for desmin (Takase S, Leo M. A., Nouchi T, Lieber C. S. Desmin distinguishes fat-storing cells from myofibroblasts, smooth muscle cells and fibroblasts in the rat. J. Hepatol. 1988; 6: 267-276), as described in Li et al., (supra, 1992). Cell cultures were incubated in a serum-free medium (with or without 175 $\mu$mol/L acetaldehyde) in airtight 35 mm culture dishes with 50 $\mu$g/ml ascorbic acid and 100 $\mu$g/ml $\beta$-aminoproprionitrile for 24 hours at 37° C. To some dishes, the following were also added: 10 $\mu$M of DLPC, LPPC, dioleoyl-PC, diarachidonoyl-PC, distearoyl-PC, dilauroyl-PC, dilinoleoyl-phosphatidyl-ethanolamine, choline, and 20 $\mu$M of linoleate or arachidonate purchased from Sigma Chemical Co. (St. Louis, Mo.) or Avanti Polar Lipids, Inc. (Alabaster, Ala.). Collagenase activity in the lipocyte culture medium was measured as described by Hu, Crombie and Franzblau (Hu C. L., Crombie G, Franzblau C. A new assay for collagenolytic activity. Anal. Biochem. 1978; 88: 638-643), with modifications reported in Li et al., (supra, 1992).

RESULTS

In Vivo Study. In the animals fed the PC-supplemented diet, the controls had normal livers, whereas the alcohol-fed animals developed significant hepatic steatosis, obvious by light microscopy, but no septal fibrosis or cirrhosis. By contrast, 8 to 10 animals given the same amount of alcohol without PC developed septal fibrosis (or even full cirrhosis in one). The difference was highly significant ($p < 0.001$ by $x^2$ test). The transformation of lipocytes to transitional cells in alcohol-fed baboons was decreased from 73% to 38% (p<0.01) after feeding of the PC-enriched diet.

In vitro Studies. Pure DLPC increased collagenase activity by 60% to 77% (measured in the media of cultured lipocytes) in the presence as well as in the absence of acetaldehyde (Table 1). A similar increase was observed when we used, in vitro, the PC preparation fed in vivo (containing 40% to 52% of DLPC); when measured in cells plus media, collagenase activity increased by 130% (p<0.001). By contrast, none of the other compounds tested (including LPPC) had an effect on collagenase activity (Table 1).

Thus, the invention encompasses pharmaceuticals containing an effective amount of substantially pure dilinoleoylphosphatidylcholine (DLPC) to prevent or treat cirrhosis or fibrosis of the liver. This amounts to about 1 to 3 grams per day, preferably about 2 grams for an adult 70-kilogram person. Most generally the dosages are administered over a period of years and are particularly effective in administration to heavy drinkers for the prevention of cirrhosis. The invention also encompasses methods for treating or preventing cirrhosis.

TABLE 1

Collagenase Activity in Media of Fat-storing Cells (% of Control). Fat-storing cells were incubated with or without acetaldehyde and collagenase activity was measured as described under Methods.

| | | Revised collagen without acetaldehyde | | | Desirable with acetaldehyde | | |
| --- | --- | --- | --- | --- | --- | --- | --- |
| | | n | $\bar{X}$ | SEM | n | $\bar{X}$ | SEM |
| Control | | 10 | 100% | | 10 | 99.3 | 5.5 |
| Phosphatidylcholine (dilinoleoyl) | (10 $\mu$M) | 12 | 160.9* | 16.4 | 13 | 177.2* | 16.7 |
| Phosphatidylcholine (linoleoyl-palmitoyl) | (10 $\mu$M) | 14 | 99 | 8.7 | 14 | 96.8 | 8.9 |
| Phosphatidylcholine (dioleoyl) | (10 $\mu$M) | 5 | 89.5 | 7.7 | 4 | 104.5 | 12.8 |
| Phosphatidylcholine (diarachidonoyl) | (10 $\mu$M) | 5 | 91.5 | 6.3 | 4 | 99.3 | 4.8 |
| Phosphatidylcholine (dilauroyl) | (10 $\mu$M) | 15 | 91.8 | 9.5 | 15 | 94.4 | 5.5 |
| Phosphatidylcholine (distearoyl) | (10 $\mu$M) | 6 | 102.3 | 10.9 | 6 | 87.9 | 11.9 |
| Phosphatidyl ethanolamine (dilinoleoyl) | (10 $\mu$M) | 7 | 118.4 | 5.7 | 7 | 113.1 | 8.4 |
| Linoleic acid | (20 $\mu$M) | 14 | 90.1 | 10.2 | 14 | 90.0 | 6.6 |
| Arachidonic acid | (20 $\mu$M) | 5 | 114.8 | 9.1 | 5 | 103.9 | 8.25 |
| Choline | (10 $\mu$M) | 7 | 97.8 | 6.3 | 7 | 113.4 | 5.6 |

*p < 0.001 (vs control)

What is claimed is:

1. A method for preventing or treating cirrhosis of the liver in a mammal in need of cirrhosis prevention or treatment comprising administering an effective cirrhosis-preventing amount of dilinoleoylphosphatidylcholine (DLPC).

2. A method according to claim 1 wherein the amount of DLPC is about 1 to 3 grams daily of substantially pure DLPC.

3. A method for protecting against alcoholic cirrhosis which comprises administering the compound of claim 1 to an alcoholic.

* * * * *